United States Patent
Choucair et al.

(10) Patent No.: US 10,264,984 B2
(45) Date of Patent: Apr. 23, 2019

(54) NON-INVASIVE CARDIOVASCULAR MONITORING DEVICE

(71) Applicants: Maged Choucair, Dearborn Heights, MI (US); Thierry Rolina, Ann Arbor, MI (US)

(72) Inventors: Maged Choucair, Dearborn Heights, MI (US); Thierry Rolina, Ann Arbor, MI (US)

(*) Notice: Subject to any disclaimer, the term of this patent is extended or adjusted under 35 U.S.C. 154(b) by 626 days.

(21) Appl. No.: 14/839,466

(22) Filed: Aug. 28, 2015

(65) Prior Publication Data
US 2017/0055854 A1 Mar. 2, 2017

(51) Int. Cl.
*A61B 5/02* (2006.01)
*A61B 5/021* (2006.01)
(Continued)

(52) U.S. Cl.
CPC .......... *A61B 5/02141* (2013.01); *A61B 5/022* (2013.01); *A61B 5/0205* (2013.01); *A61B 5/6824* (2013.01); *A61B 5/6826* (2013.01); *A61B 5/6831* (2013.01); *A61B 5/6833* (2013.01); *A61B 5/6838* (2013.01); *G01G 19/50* (2013.01); *A61B 2562/0261* (2013.01); *A61B 2562/168* (2013.01)

(58) Field of Classification Search
CPC ....... A61B 5/024; A61B 5/025; A61B 5/0225; A61B 5/02116; A61B 5/02444; A61B 5/6816; A61B 5/6826; A61B 5/6838; A61B 5/02208; A61B 2562/0261
See application file for complete search history.

(56) References Cited

U.S. PATENT DOCUMENTS 2,549,049 A 4/1951 Bierman
3,278,881 A * 10/1966 Anderson ............. G01L 1/2206
29/621.1
(Continued)

FOREIGN PATENT DOCUMENTS

WO 9813674 A1 4/1998

OTHER PUBLICATIONS

Emily Singer, A Wristwatch That Monitors Blood Pressure, Jun. 30, 2011, http://www.technologyreview.com/news/424539/a-wristwatch-that-monitors-blood-pressure/, 1 pg.
(Continued)

*Primary Examiner* — Eric J Messersmith
(74) *Attorney, Agent, or Firm* — Brooks Kushman P.C.

(57) ABSTRACT

A cardiovascular monitoring system includes a sensor assembly and a controller. The sensor assembly includes a membrane enclosing a viscous fluid, a substrate immersed in the viscous fluid, and at least one strain gauge mounted with the substrate. The strain gauge is configured to detect bending of the substrate due to changes in capillary blood pressure of a person in contact with the membrane at less than 50 mmHg contact pressure and to output a signal indicative of the changes. The controller may be configured to output a change in mean arterial pressure of the person based on a profile of the signal that is associated with a heartbeat of the person. Also, the controller may be configured to output the mean arterial pressure based on a weight signal indicative of a weight of the person and the profile of the signal associated with the heartbeat.

11 Claims, 7 Drawing Sheets

(51) Int. Cl.
   *A61B 5/0205*   (2006.01)
   *A61B 5/00*     (2006.01)
   *A61B 5/022*    (2006.01)
   *G01G 19/50*    (2006.01)

(56) References Cited

U.S. PATENT DOCUMENTS

| | | |
|---|---|---|
| 5,267,566 A | 12/1993 | Choucair et al. |
| 6,398,740 B1 | 6/2002 | Lavery et al. |
| 7,118,534 B2 | 10/2006 | Ward et al. |
| 7,283,870 B2 | 10/2007 | Kaiser et al. |
| 7,691,068 B2 | 4/2010 | Felder et al. |
| 8,585,602 B2 | 11/2013 | Crabtree et al. |
| 2006/0206031 A1* | 9/2006 | Hasegawa .......... A61B 5/02116 600/490 |
| 2011/0054330 A1* | 3/2011 | Pfeiffer .............. A61B 5/02225 600/490 |
| 2013/0310700 A1 | 11/2013 | Wiard et al. |

OTHER PUBLICATIONS

Wristband Revolutionises Blood Pressure Measurement, EMPA Materials Science & Technology, Jun. 12, 2013, Dubendorf, St. Gallen, pp. 1-3.

Maged N. Choucair, A Study Into Design and Development of Noninvasive Blood Pressure Monitoring Device, Thesis for University of Detroit, 1991, Detroit, Michigan, 170 pgs.

\* cited by examiner

NON-INVASIVE CARDIOVASCULAR MONITORING DEVICE

TECHNICAL FIELD

This disclosure relates to systems and methods of non-invasively measuring cardiovascular characteristics.

BACKGROUND

In a human body, there are over 100 trillion cells, which communicate with each other by low electromagnetic signals and through biochemical reactions. Each cell exchanges nutrition, wastes, and other materials with a blood stream at specific ranges of blood pressure, flow rate and temperature. The cardiovascular system of the human body is a highly complex control system that controls communication signals and biochemical reactions for the cells. Also, the cardiovascular system is controlled by demands of the cells, hormones in the blood stream, and an augmentation pressure, which is a reflection of blood pressure waveform signals at branching nodes of arterials. Hence, the cardiovascular system mitigates and controls any sudden changes in the blood pressure.

SUMMARY

A blood pressure sensor assembly includes a membrane having a surface configured for contact with a body of a patient, a liquid surrounded by the membrane and having a viscosity greater than 0.008 Poise, a substrate immersed in the liquid, and a strain gauge mounted with the substrate such that changes in a contact pressure between the membrane and body due to changes in blood pressure associated with the body result in flexion of the substrate and changes in an output signal of the strain gauge.

A blood pressure sensor assembly includes a gel, a base supporting the gel and configured to hold the gel against a person, and a strain gauge assembly supported by the base, embedded in the gel, and configured to flex in response to pressure waves propagated by the gel due to changes in blood pressure associated with the person, and to output a signal indicative of the changes in blood pressure.

A cardiovascular monitoring system includes a sensor assembly and a controller. The sensor assembly includes a membrane, a viscous fluid enclosed by the membrane, a substrate immersed in the viscous fluid, and at least one strain gauge. The at least one strain gauge is mounted with the substrate and configured to detect bending of the substrate due to changes in capillary blood pressure of a person in contact with the membrane at a contact pressure less than 50 mmHg, and to output a signal indicative of the changes. The controller is configured to output a change in mean arterial pressure of the person based on a profile of the signal that is associated with a heartbeat of the person.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The embodiments of the present disclosure generally provide for a plurality of circuits or other electrical devices. All references to the circuits and other electrical devices and the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EE- PROM), or other suitable variants thereof) and software which co-act with one another to perform operation(s) disclosed herein. In addition, any one or more of the electric devices may be configured to execute a computer-program that is embodied in a non-transitory computer readable medium that is programmed to perform any number of the functions as disclosed.

There is a need for continuous non-invasive blood pressure monitoring in hospitals, outpatient care centers, and individual homes in which patients are being medically monitored. In a hospital, the need is especially strong in an Intensive Care Unit (ICU) and Critical Care Unit (CCU). A human body is generally capable of coping with stable conditions. For example, a stable but high blood pressure of a person is (of course within a certain range) not as alarming as large fluctuations in blood pressure during a given time period. Hence, the blood variations are more important than the initial readings of the blood pressure. The blood pressure variations may create stress variations in the artery walls that may be followed by fatigue and sometimes failure in the arteries. The use of tonometry to measure blood pressure has been investigated in the past with very limited success. Here, a new approach will be illustrated to overcome the previous deficiencies.

Preliminary studies led to more than one possible solution for the main problems in the tonometry method—finding the artery, keeping the transducer in the right position above the artery, and calibrating the device to get accurate readings.

To solve the problem of finding the artery and keeping the transducer in the right position above the artery, a mathematical model of the transducer over the artery was explored. Based on this model, improvements to some concerns with tonometry based on the mathematical model will be discussed. For example, the use of a transducer over a finger nail has produced good results in regard to the skin motion. Skin motion includes 1) external skin motion due to hand movement, and 2) skin motion due to artery escaping external pressure. To minimize the effect of skin motion, the transducer is placed away from an artery (e.g., fingertip, ear lobe, nose, or other location supplied by arterioles and capillary vessels). The use of a semiconductor strain gauge may allow amplification to signals as a signal produced by a pressure transducer from arterioles and capillary vessels is quite small.

Regarding calibration of the sensor assembly, note that this problem is not too serious because physicians do not require an absolute blood pressure measurement, but rather they are looking for exact variations of that pressure. Therefore, if a device can be developed which can measure the blood pressure variations in an accurate and faithful way, then physicians will tolerate from 10% to 20% error in the absolute readings of the blood pressure. A magnitude of error in the range of 10% to 20% is similar to that of the BP cuff method (sphygmomanometer). This may be improved via the use of an automated BP checking device for a periodical check, for example, every hour, and to correct the tonometer in case of errors. Another method to solve the calibration problem is to study further the relationship between the closing of the blood flow and the amplitude of the transducer readings when that transducer is used on the finger. It was observed in preliminary work in the laboratory that when the transducer was used on the finger and a cuff was used on the same arm, during the application of high external pressure on the arm the reading of the transducer was zero (at the same time no Korotkoff sound could be heard). After releasing the outside pressure gradually, at certain pressure a small amplitude of transducer readings began to appear at the time the appearance of Korotkoff sound. Note also that the amplitude of the readings of the transducer continued to increase as the outside pressure slowly decreased. Consequently when using this procedure, the systolic and diastolic pressures correspond respectively to the outside pressures at the first appearance of the transducer readings and to the first point when the readings become constant.

Design one uses a mechanical transducer also referred to as a sensor or strain gauge sensor that has a needle (rider) which rests on the artery. The contact area between the rider and the artery is about one millimeter in diameter. The problems associated with the use of a device on the wrist include the difficulty in locating the artery, the difficulty in keeping the rider of the transducer above the artery after motion of the hand or the fingers, and a good and easy procedure for calibrating the device.

A solution to the above problems includes confinement of the wrist into a channel type seat filled with plaster of Paris for comfortable resting of the wrist in the channel and to render the wrist immobile. One advantage, since the transducer can fall freely to touch the wrist, is that the weight will apply a constant force on the artery. However, this system might not be able to eliminate the motion of the artery, which will try to escape the high pressure due to the transducer's rider application.

For the calibration, a procedure may be tried where the patient elevates the arm by a known distance. The difference in pressure due to the elevation changes can be computed using hydrostatic pressure principles. In this manner, the calculated pressure changes can be used to calibrate the device, knowing that the changes in the device readings are directly proportional to the changes in the blood pressure. This procedure may fail due to the correction that the human body does to react to the blood pressure changes. This device maybe used not only on the wrist but also on the finger.

Design two includes the application of the principle of tonometry by pressing a piece of tube against the finger. The tube may be constructed of a pliable material such as rubber, plastic or a polymer. The tube was connected on one end to a pressure transducer while the other end was closed. Studies of the data of many experiments on this device showed the output wave was quite stable for long period of use. However, the shape of the pressure signal was not of the right shape. To correct the shape of the signal from design two, the following procedures could be used:

First, the length of the tube should be varied to see the effect on the signal shape. The signal from the blood pressure will propagate in the tube in both directions (towards and away from the pressure transducer), and then the wave will strike the closed end of the tube and get reflected with opposite sign. The reflected wave will interfere with subsequent waves. Consequently, the two waves subtract one from the other in such a way that the resultant signal is modified to a new amplitude and therefore a new shape. This requires that the tube length and shape be tuned based on the liquid and the pliability of the tube.

Second, the diameter of the tube should vary to determine if that will make any difference. The reason for this recommendation is that the size of the tube used in that experiment (about ¼ inch in diameter) is very large compared to the diameter of a capillary blood vessel, so the wave might be transformed and dissipated before reaching the pressure transducer. It may advisable to try different elasticity, flexibility and pliability of the tube by using different materials.

In the event of an inaccuracy of the above mentioned calibration procedures, the cuff device can be for an initial calibration. Moreover, since new automated cuff devices have been developed lately, they can be used for periodic check on the calibration of this device using a computer program.

Another method of calibration includes outside pressure applied by a cuff on the arm until the transducer reading is zero, then the outside pressure is released slowly, until the reading starts to appear at which point the outside pressure will be equal to the systolic pressure and, when the reading becomes constant (independent of outside pressure) then the corresponding outside pressure will be equal to diastolic pressure.

Design three applies the principle of tonometry using strain gages. The design was to place two strain gages (gage type: WK-13-125AD-350) on a piece of plastic (one gage on each side of the plastic), then form it into a wristband fitting over the radial artery. The strain gages were connected to a Wheatstone bridge, the bridge power and signal amplification means. The signal from the bridge amplifier was fed to a low-pass filter, which allows the passage of low frequency signals (less than 20 hertz) and amplifies the signal about 100 times. Then the signals were displayed on a recorder (or an oscilloscope). The above setup gave good signals, but it was found, as in the previous investigations, that their magnitudes depend on the proximity to the artery.

The setup for design three has many advantages over design one and two; it can be made of portable size. This is because the strain gage has a very small size and a very light weight compared to other devices. It can be used on many places on the human body. For example, patients can use this device on the finger tip, on the ear lobe, on the nose, or on the fingernail. It is expected to get the best results when the device is placed on the fingernail, because the nail is the most stable part of the human body where that device can be placed and the area of contact between the device and the nail can be kept constant. The outside applied pressure on the human body could be kept very small, therefore, it is possible to measure the blood pressure with little disturbance for the blood flow. This fact will give more accurate and faithful measurements. The use of semiconductor strain gages may be employed to measure very small pressures, such as pressures on a fingernail, with acceptable precision. It may be advisable to design this structure in such a way that measurement of one directional motion is allowed for the system. In which the strain gages should be placed on a plate, such as a flexible piece of plastic, then the plate is attached to a clamp in the form of a clothes pin. The pressure on the clamp should be sufficient to keep it at the attachment point. This clamp can be used on the ear lobe, or for other parts of the body and for each the form should be modified to fit the particular shape.

The measurement of one-directional motion of the device is usually perpendicular to the body surface. This one-directional motion measurement may eliminate a significant amount of the body motion. Usually the skin motion starts at some muscle movement away from the device, then as the skin movement propagates along the skin surface until that wave reaches the body below the device, the skin motion has little or no effect on the readings of the device.

Also, it may be desirable to use design three away from the artery even though the device has one-directional motion. Along with the reasons mentioned above, is the fact that the flow of the blood in the artery adds a tangential component, in the direction of the flow, to the force generated by the blood pressure. This tangential component will prevent the force in the blood from being perpendicular to the artery wall. The result of the tangential component is that the device may oscillate back and forth in a continuous motion. This oscillation may depend on the amplitude of the blood pressure and on the velocity of the blood flow. The amplitude and flow characteristics may causes instability in the output of the device. However, for the case of using the device on capillary vessels, the blood flow is in all directions. The flow of capillaries and the fact that the blood velocity in capillaries is very small compared to the velocity in the artery, may result in increased stability to the output of the device when the sensor is placed to measure blood pressure away from the arteries.

Other advantages to this solution are that the cost of design three is low compared to the direct method expenses. This will give the device a broader application in case of success. The calibration of design three may use the same procedures as recommended as for the other devices above. A further advantage is the size of implementation, as design three may be made small such that is may be used on an ear lobe, a finger, or in an adhesive pad. Design three may be implemented having a very light weight and be readily capable of being used as a portable device. This includes being easy and quick to install, usually within a few seconds. This device may be easy for maintenance and debugging problems when used in the field such as in the detection of malfunctioning. This design may be comfortable in its implementation thus allowing it to be worn by a patient for a long time. And may be implemented having little or no allergic effect on patient.

Design three is based on a tonometric method. Tonometry is based on the principle that when a curved surface of a pressure vessel is flattened by a rigid plane, the force on the plane is equal to the pressure multiplied by the area of the contact. Tonometry has been used successfully in the measurement of intraocular pressure. Here, the use of tonometry on arterioles and capillary vessels is seen to have increased accuracy over tonometry on arteries. And, the use of a device which picks up one directional movement, perpendicular to the flesh surface, to minimize the effect of flesh movement on the blood pressure reading is advantageous.

The use of tonometry on arterioles and capillary vessels resolves one problem encountered in applying tonometry to arterial blood pressure measurements: finding and maintaining the sensor over the artery. Design three offers an easy solution for this problem, namely, it is not necessary to locate the artery when using this device, as design three should be used away from artery.

The second aspect to the application of arterial tonometry is to keep the device rider on the artery. The artery usually tries to escape from pressurized positions to a less pressurized position, commonly seen as rolling veins and arteries. The use of tonometry away from arteries has the advantage that arterioles and capillary vessels have very few muscles in their walls compared to arteries. This reduced muscular structure results in a minimized movement when pressurized. In addition, the size of the arteriole or capillary is less than that of the artery, and the associated movement of the arteriole or capillary is smaller than the artery when pressurized. Moreover, the force due to a pulse in arterioles and capillaries is much smaller than the force in the arteries. Adding to this fact that the force per unit area exerted by the device on arterioles or capillaries is much less than the one exerted on the arteries, then it may be concluded that the movement of arterioles and capillaries to escape high outside pressure is much smaller than the one for arteries. Furthermore, while the readings of blood pressure depend on the vicinity of the device to the artery as any flesh movement will shift the device and affect the readings of blood pressure, this problem is minimized when the device is used away from the artery.

An inherent step in the blood pressure measurement procedure is calibrating the device that must be performed in each case the sensor is used. A known method of using a blood pressure cuff and stethoscope to determine the korotkoff sounds is one method of measuring an initial reading for the calibration. The accuracy of the sensor system cannot be better than that of the cuff method. The accuracy of the cuff method has been studied by a number of investigators and there is a general agreement that it is no better than 10% to 20%, but it has been used for many years by a great number of practicing physicians providing a feeling of confidence among the professions. Furthermore, physicians pointed out that the absolute values are not as important as the changes in blood pressure. It is felt, therefore, that the use of the cuff method in the calibration procedure is justified and will be accepted by the medical profession. When the transducer is used on the ear lobe, or on the nose, the cuff measurement will have no effect on the reading, hence the calibration procedure can be quite simple. The transducer is attached to the ear lobe (or on the nose) and the standard auscultatory pressure reading is taken. The amplitude of the signal is then adjusted so the top of the curve shows the systolic and the bottom the diastolic value of the blood pressure. It is recommended that the transducer be checked periodically thereafter to assure its continued proper operation. For the transducer positioned on the finger or on the fingernail, the calibration procedure must be modified since the application of pressure in the cuff will stop the blood flow to the finger and the signal will disappear.

The use of two strain gages on opposite sides of a platform coupled to a Wheatstone bridge was used to compensate for temperature variations. The platform is also referred to as an arm, a base or a backing. The changes in temperature between the two strain gages may produce an instability of a reading or output of the strain gauge in the presence of even a small convection current. A laboratory experiment was performed in which light blowing on the strain gage or movement of the strain gauge proximate to a warm body caused drastic shifts in the output of the strain gauge. As a result, the strain gages were adhered to a hard plastic platform, such as acrylic, to insulate them thermally from the surroundings. Although a hard plastic was used other materials or composites may be used to insulate the strain gauge from temperature variations. And in production, the strain gauge may be embedded in the platform to reduce any adhesive concerns. To address humidity concerns, the use of waterproof coatings may be used to protect the strain gauge and sensor assembly.

Regarding the linearity of blood pressure variations in blood vessels, two different approaches were conducted to validate the linearity assumption for the blood pressure variations in different blood vessels. The result of these approaches was that errors between blood pressure in arteries, arterioles and capillaries was less than 0.5% when measured using a sensor assembly including a strain gauge.

The first approach is assessing compliance and resistance in arteries. Compliance is an index of the elasticity such as the ability of large artery (aorta) to distend and increase volume with increasing blood pressure. An increase in the age and in systolic blood pressure can cause decrease in arterial compliance. The main function of artery compliance is to minimize the blood flow fluctuation by acting as an elastic pressure reservoir for the blood. And resistance is when the arteries and arterioles contract or dilate to regulate the blood pressure.

The second approach is assessing sympathetic tone in arterioles. Here, the sympathetic nervous system is activated such as in the fight or flight mode. When the nerve connects with muscles surrounding the blood pressure vessel then norepinephrine is released. When norepinephrine binds to alpha 1 receptors then it will cause the arteriole to constrict. But, when norepinephrine binds to beta 2 receptors then it will cause the arteriole to dilate.

Other factors include hormones, endothelium, metabolic factors, and blood waveform reflection at arteries branching. Hormones regulate the diameter of arterioles that receive hormonal autonomic nervous system innervation in response to various circulating hormones. The endothelium lines all blood-contacting surfaces, including arterioles, arteries, veins, capillaries, and heart chambers. There is direct electrical and chemical communication via gap junctions between the endothelial cells and the vascular smooth muscle. Based on some metabolic functions, arterioles might contract or dilate to regulate the blood flow to certain body tissues. Blood pressure waveform reflection might impact the blood pressure device readings depending on the arterial stiffness.

Figure 1A:
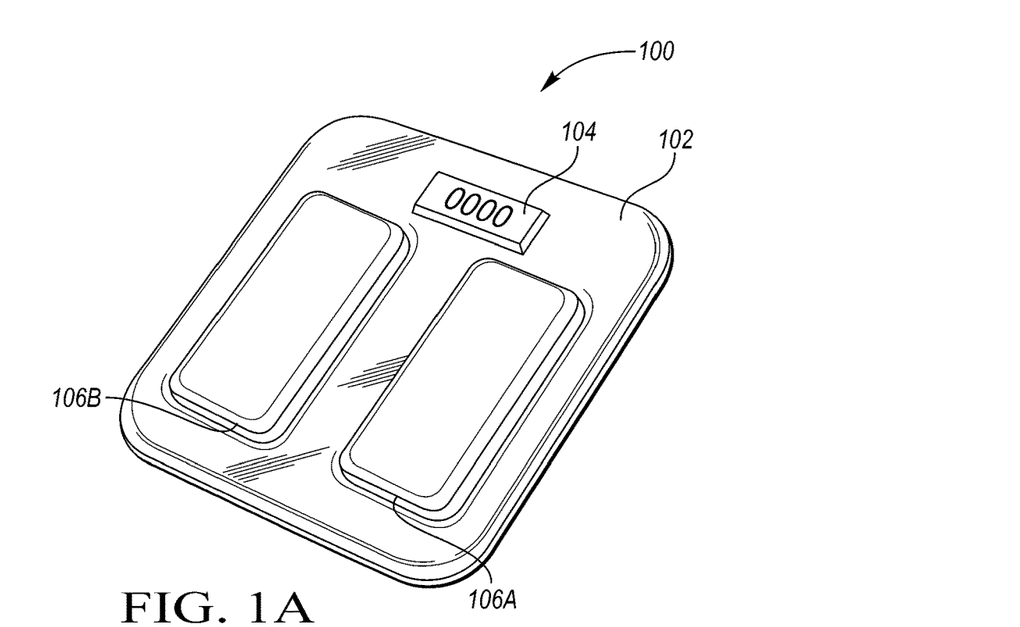
FIGS. 1A and 1B are exemplary illustrations of a scale including a sensor assembly configured to measure cardiovascular characteristics.

FIG. 1A is an exemplary illustration of scale 100 including at least one sensor assembly 106 configured to measure cardiovascular characteristics. The scale 100 includes a platform 102, a display 104, and at least one sensor assembly 106. The scale 100 is shown generally square, however, the scale 100 may be rectangular, circular, oval, or any other shape such that it is able to accommodate an area of human feet standing on the scale 100. The platform 102 may be a rigid or semi-rigid platform made of materials including plastic, glass, and metal. The platform is sized and configured to support the display 104 and at least one sensor assembly 106. The display 104 may be analog or digital. The display 104 may be electrically coupled to a controller that receives signals from the at least one sensor assembly 106, processes the signals, and outputs the signals via the display 104. The at least one sensor assembly 106 may include at least one strain gauge configured to measure a pressure of a fluid in the sensor assembly 106. The sensor assembly 106 may be configured as two individual pads (106A and 106B) and the two individual pads (106A and 106B) may be coupled such that the two individual pads (106A and 106B) output at least one signal indicative of a change in a mean arterial pressure. The coupling may be achieved by connecting the two individual pads (106A and 106B) by a small tube in the range of 5 mm diameter. The tube could be equipped with a valve. The main function of the tube is to make the two pads work as one continuous pad when the valve is open. When the valve is closed, the two pads work independently. In the case of the two pads functioning as one continuous pad, the sensor in pad 106A or 106B will always experience the total weight of the patient. The pressure in the liquid in each pad will be identical (proportional to the total weight of the patient). In the case of the two pads functioning as two independent pads, there will be a distribution of weight on pads 106A or 106B depending on how the patient balances the total weight between the 2 feet. This approach can be used in the calibration (training) of the device. Control of each individual pad can be achieved by filling the tube with a spongy material which in turn will prevent any interference between the 2 pads. The two individual pads (106A and 106B) each may be of a size and shape to accommodate a sole of an average human foot standing on the sensor assembly 106. The sensor assembly 106 is shown rectangular however, the sensor assembly 106 may be circular, oval, shaped like a foot, or any other shape such that it is able to accommodate an area of human feet standing on the assembly 106

Figure 1B:
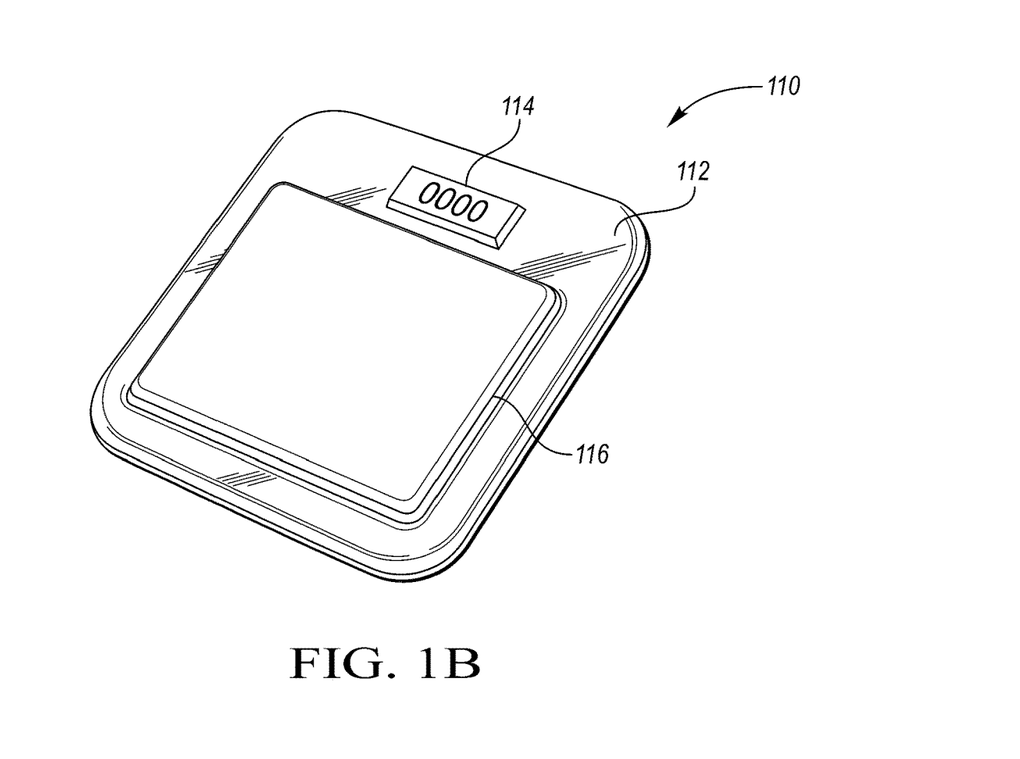

FIG. 1B is an exemplary illustration of scale 110 including at least one sensor assembly 116 configured to measure cardiovascular characteristics. The scale 110 includes a platform 112, a display 114, and at least one sensor assembly 116. The scale 110 is shown generally square, however, the scale 110 may be rectangular, circular, oval, or any other shape such that it is able to accommodate an area of human feet standing on the scale 110. The platform 112 may be a rigid or semi-rigid platform made of materials including plastic, glass, and metal. The platform is sized and configured to support the display 114 and at least one sensor assembly 116. The display 114 may be analog or digital. The display 114 may be electrically coupled to a controller that receives signals from the at least one sensor assembly 116, processes the signals, and outputs the signals via the display 114. The at least one sensor assembly 116 may include at least one strain gauge configured to measure a pressure of a fluid in the sensor assembly 116. The sensor assembly 116 may be configured as a single pad sized and shaped to accommodate the soles of two human feet of an individual standing on the sensor assembly 116. The sensor assembly 116 may be configured to output at least one signal indicative of a change in a mean arterial pressure. The sensor assembly 116 is shown rectangular, however, the sensor assembly 116 may be circular, oval, shaped like a foot, or any other shape such that it is able to accommodate an area of human feet standing on the assembly 116

For example, a patient would stand with bare feet on the scale 110 and specifically on the pad 116. Based on the contact of the bare feet with the pad 116 and the weight of the patient, the scale 110 would be calculating the mean arterial pressure (MAP). This calculation is based on the body weight for the sensor under the foot (which is proportional to the pressure in the bladder under the foot). If the scale 110 was being used in conjunction with an alternative blood pressure monitoring device (such as a cuff or finger monitor), the MAP pressure values should be the same for both sensors (the finger sensor and the foot sensor) for the same heartbeat. The use of two sensors (such as a finger and foot, finger and opposite arm cuff, or cuff and foot) will significantly reduce the errors of the change in volume of the finger, or the change of the flesh flexibility (stiffness) of the finger. A pulsating waveform and change in blood pressure (ΔP which is systolic pressure—diastolic pressure) may be taken from the either sensor. Here, the MAP pressure may be calculated based on the area under the pulsating curve and the geometric shape index of the pulsating curve. This can be done as described below. Also, while the patient is standing on the bathroom scale 110, the patient may do some selected exercises that may change the force exerted on the scale 110 such as taking consecutive deep breaths or consecutive Valsalva maneuvers. Also, in the case of the design of a scale 100 having two independent pads 106 as shown in FIG. 1A, the patient may change the applied force on one pad from a fraction of a force due to the body weight to a force of roughly double the body weight. For different force and patients, the area under the pulsating curve as well as the geometric shape index may be calculated. Hence, we can relate MAP pressure to the area under the curve and the geometric shape index.

The bathroom scale method of cardiovascular characteristic measurement is such that a sensor is placed under at least one foot, then the mean arterial pressure (MAP) is is correlated to a force based on the body weight of the patient. This can be expressed by equation 1.

$$Pd = \text{MAP} - \Delta P/3 \tag{1}$$

In which Pd=diastolic pressure, and ΔP=systolic pressure−diastolic pressure. ΔP may be read with high precision from the device reading because it is a difference of two values; as such substantially all of the errors will cancel out. The mean arterial pressure (MAP) may be calculated many ways. One method is to calculate a mean arterial pressure based on the weight of a patient (MAP_w) as shown in equation 2.

$$\text{MAP}\_w = C1 * Pwt + C2 * \text{Height} + C3 * \text{Age} \tag{2}$$

In which Pwt is the pressure due to weight of the patient. The Pwt may be based on the pressure of the liquid inside the sensor. C1, C2, C3 are coefficients that may be calibrated using a known method of determine a blood pressure, (e.g, sphygmometer).

Another method of calculation is the mean arterial pressure of the center of mass of the area under the curve (MAP_c). The calculation of MAP_c will be discussed further when describing FIGS. 8A and 8B.

Figure 2:
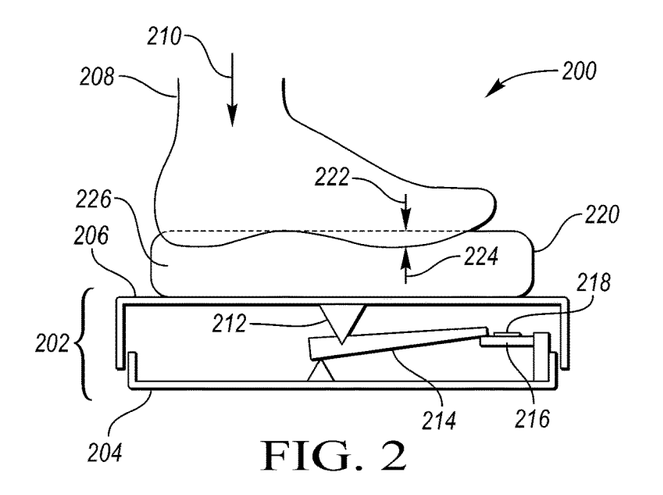
FIG. 2 is an exemplary cross-sectional view of a scale illustrating an upper section where the person will step and a bottom section showing the sensor assembly.

FIG. 2 is an exemplary cross-sectional view of a scale 200 illustrating an upper section where the person will step and a bottom section 202 showing the sensor assembly. Here, the bottom section 202 of the scale is configured to output a signal indicative of a force 210 applied to the top platform 206 while the bottom platform 204 is generally held constant (such as being placed on the ground or a floor). A foot 208 of a patient exerts a portion of a weight force 210 of the patient on a fluid 226 enclosed within a bladder 220 also referred to as a pad. A fluid filled bladder includes the combination of the fluid 226 and the bladder 220. The force 210 generates a contact pressure 222 from the foot 208 on the bladder 220. The weight force 210 is generally constant. The contact pressure 222 also includes small variations or pulses of changes in pressure due to blood flow within the body. These small variations in pressure are transmitted from the foot 208 more specifically, the bottom of a bare foot to the bladder 220 and the fluid 226 within the bladder 220. A sensor may then be used to measure the changes in pressure of the fluid 226. The bladder 220 reacts with a fluid pressure 224 on the foot (pressure 222 is equal to pressure 224). The bladder 220 is filled with a liquid with characteristics similar to that of human blood in constitution and physical properties like viscosity and density. Viscosity has the SI units Pascal seconds (Pa s) that is also called Poiseuille. In this application, all viscosity measurements will be based on ASTM D 2161-66(1971) viscosity methods. A more common representation is dyne sec/cm2 which is called Poise. One Pa s is equal to 10 Poise. The viscosity of air at 20 degrees Celsius is approximately 0.0002 Poise, the viscosity of water at 20 C is approximately 0.01 Poise and the viscosity of blood at body temperature is approximately 0.03 Poise. Also, bladder 220 may contain a pressure sensor (not shown on FIG. 2) or may be coupled to the pressure sensor. A scale 202, which supports the bladder 220, is configured to output a force signal based on a force applied to the platform 206 indicative of a weight on the platform 206. The scale 202 should have a precision of 0.05 pound or better. The weight force 210 is also transferred to a fulcrum 212 which exerts a pressure on a lever 214. The lever 214 then exerts a force on a sensor assembly 216 causing it to bend. The amount of bending (such as expansion of one surface of the assembly or compression of the other side of the assembly) may be detected using a strain gauge 218 coupled to the assembly.

Figure 3:
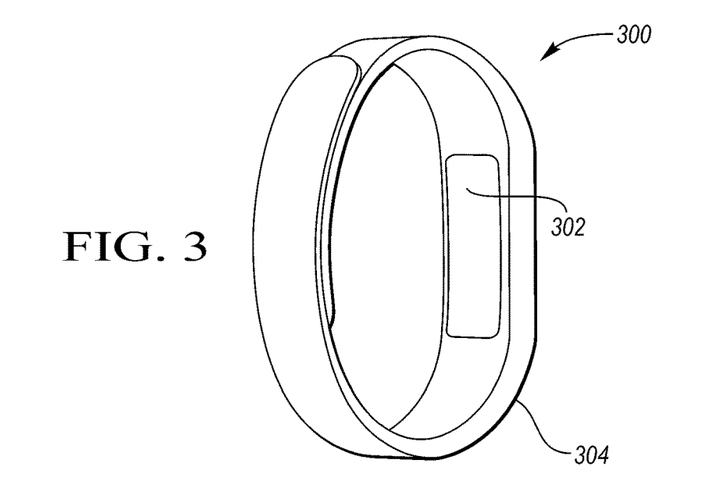
FIG. 3 is a personal wearable device including a sensor assembly configured to measure cardiovascular characteristics.

FIG. 3 is a personal wearable device 300 including a sensor assembly 302 configured to measure cardiovascular characteristics. This personal wearable device 300 is shown having a band 304. The band may be sized and shaped to be worn on a wrist, finger, ankle, or as a headband. Although the personal wearable device 300 is shown with a band 304, a personal wearable device may also be integrated into a shirt such as in a collar, lapel, or positioned to contact the chest or back. A personal wearable device may also include an adhesive bandage also referred to as an adhesive pad, or an adhesive contact, that may include a foam-tape backing having a gel (such as a sticky or tacky gel) to ensure excellent skin contact. The adhesive used may be designed to endure days of continuous use and associated changes in the properties of the patient's skin adhered to such as diaphoretic conditions. The adhesives may be similar to currently used adhesive electrodes. And the gel used in many current electrodes may be used as the liquid. A personal wearable device may be electrically coupled to a nurse's station for monitoring of cardiovascular characteristics. A personal wearable device may also include a battery and a RF transceiver that can wirelessly transmit a signal indicative of the blood pressure, pulse, pulse waveform, and other cardiovascular characteristics.

Figure 4:
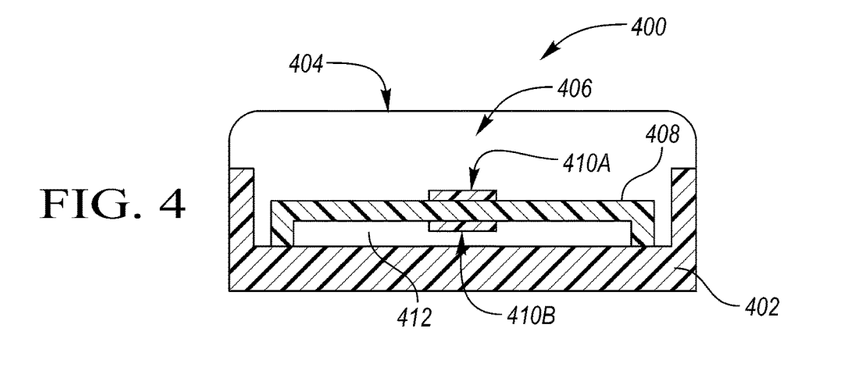
FIG. 4 is a cross-sectional view of a sensor assembly configured to measure cardiovascular characteristics.

FIG. 4 is a cross-sectional view of a sensor assembly 400 configured to measure cardiovascular characteristics. The sensor assembly 400 includes a membrane 404, a liquid 406, a plate 408, top and bottom strain gages 410A and 410B, and a bottom encasing 402. The membrane 404 also referred to as a pouch, or pad, may include a leather membrane, a rubber membrane, or a polymer membrane such as polyester, polyethylene, polyvinylidene chloride, etc. The side of the membrane 404, which contacts skin of a patient, should be of comfortable for long hours of use by the patient. The plate 408 may have a geometric shape such as a rectangular, square, or oval and may be constructed of a metal, alloy, or polymer material such as aluminum, iron, or plastic. An experiment was performed using a thin aluminum rectangle having generally the dimensions 0.4 cm by 1.5 cm and 2 mm thick. Also, a hard plastic rectangle constructed of acrylic having the dimensions 0.4 cm by 1.5 cm and 0.4 mm thick. The plate 408 could be supported by two supports constructed of the same material as that of the plate 408 such that the support forms a bridge. The use of a bridge structure may be used in many applications including use under the foot of the patient. In an alternative embodiment, the plate could be supported on one side only (cantilever type). The cantilever type may be used in many applications including use on a finger. The area 412 under the plate 408 could be filled by spongy type material to improve the deflection of the plate 408 during the use of the sensor.

The sensor assembly 400 includes at least one strain gage encompassed by the liquid 406 encased in a pad 404. The side of the pad 404 which contacts the skin of the patient should be of soft material such that it is comfortable for long hours of use by the patient. Although a single strain gauge may be used, ideally two strain gages should be coupled to the plate 408. The liquid 406 inside the sensor assembly 400 should have physical characteristics comparable to that of the human blood (regarding viscosity, density, and suspension particles). The liquid 406 has multiple advantages, For example, it can minimize the effects of skin movement by configuring the strain gauges to generate an output based on a single directional measurement of the pressure. The liquid 406 in conjunction with the membrane 404 may provide an electrical coupling with the patient such that electromagnetic and electrostatic signals on the skin may be conducted to a grounding sink in the device control box. The liquid 406 may be able to compensate for any volume change in the body part (finger, foot, ear lobe) in contact with the membrane 404. The liquid 406 may minimize the effect of blood waveform reflection by generally matching the characteristics of the body thus dampening signal.

In an alternative embodiment, the sensor assembly may not include the membrane 404 but may utilize a sticky gel as the liquid 406 such that the liquid is in direct contact with a patient's skin. This may reduce cost and provide a better transfer of the pulse waves from the flow of blood. A liquid must be chosen to have a faithful transfer in energy between the blood and liquid. The use of a liquid having a viscosity close to that of ballistic gelatin may correct the irregularities in blood waveform from Design two. Design Two has a stable baseline of blood pressure readings, but the waveform has a different shape because it is using air instead of liquid inside the sensor.

Figure 5A:
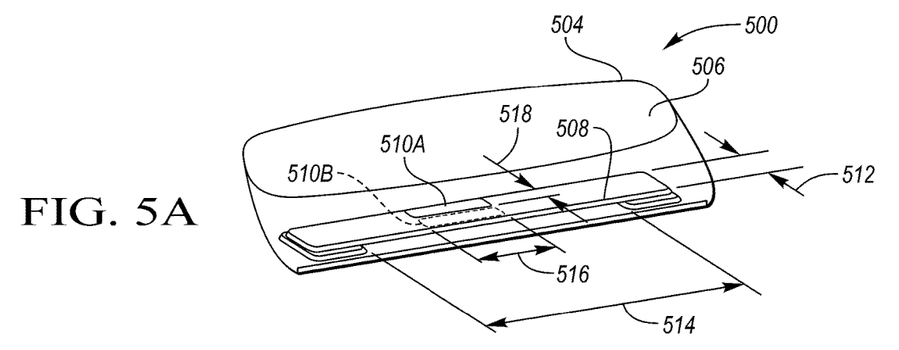
FIGS. 5A and 5B are perspective views of alternative embodiments of a sensor assembly configured to measure cardiovascular characteristics.
Figure 5B:
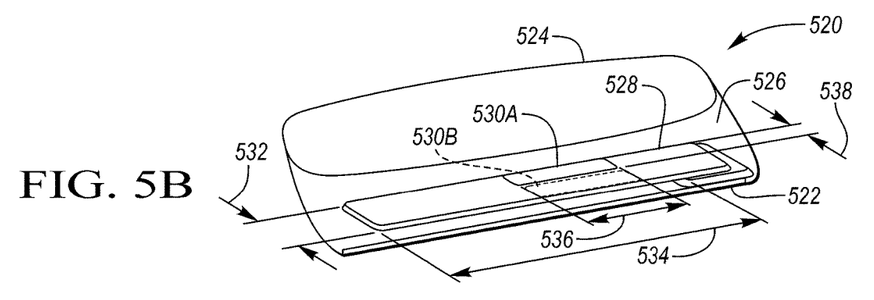

FIGS. 5A and 5B are perspective views of alternative embodiments of a sensor assembly configured to measure cardiovascular characteristics. The sensor assembly 500 includes a membrane 504, a liquid 506, a plate 508, a top strain gauge 510A, and a bottom strain gage 510B. The membrane 504 may be leather, rubber, plastic or a polymer. The membrane is configured to contact the skin of a patient. The plate 508 is shown as a thin rectangular plate and could be constructed of aluminum. The plate has a length 514, a width 512 and thickness. For example, an aluminum plate may have the following dimensions: width 512 is 0.4 cm, length 514 is 1.5 cm, and thickness is 2 mm. The plate may be constructed of hard plastic type such as acrylic having the following dimensions: width 512 is 0.4 cm, length 514 is 1.5 cm, and thickness is 0.4 mm. The strain gauge 510A may have a length 516 and a width 518. The strain gauge 510B may have similar dimensions to gauge 510A or may be of different size. The configuration of the sensor assembly 500 may be supported by a scale such as a bathroom scale to detect cardiovascular characteristics through the soles of a patient's foot. An alternative sensor assembly 520 includes a membrane 524, a liquid 526, a plate 528, and a top strain gauge 530A. A bottom strain gage 530B is very similar to the assembly 500 except that the thin rectangular plate 528 is of cantilever design or type. A cantilever design is supported on one end similar to a diving board. It could be of aluminum (width 532 is 0.4 cm, length 534 is 1.0 cm, and thickness is 2 mm), or it could be of hard plastic type such as acrylic (width 532 is 0.4 cm, length 534 is 1.0 cm, and thickness is 0.4 mm). The strain gauge 530A may have a length 536 and a width 538. The strain gauge 530B may have similar dimensions to gauge 530A or may be of different size.

In an alternative embodiment, the sensor assembly 500 and 520 may not include the membrane 504 and 524 but may utilize a sticky gel as the liquid 506 and 526 such that the liquid is in direct contact with a patient's skin. This may reduce cost and provide a better transfer of the pulse waves from the flow of blood. A liquid must be chosen to have a faithful transfer in energy between the blood and liquid. The use of a liquid having a viscosity close to that of ballistic gelatin may correct the irregularities in blood waveform.

Figure 6:
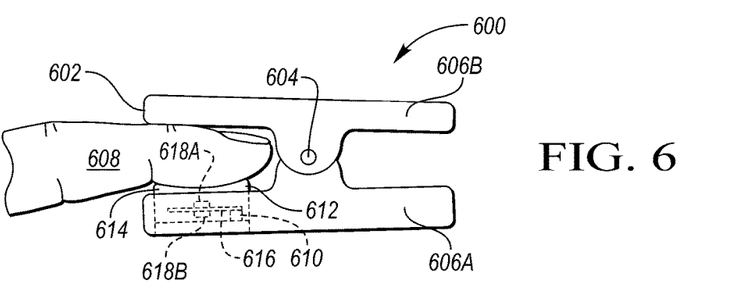
FIG. 6 is a side view of finger clip including a sensor assembly configured to measure cardiovascular characteristics.

FIG. 6 is a side view of finger clip assembly 600 including a sensor assembly configured to measure cardiovascular characteristics. The finger clip assembly 600 consists of front top jaw 602 for clamping on a patient's finger 608 in a comfortable but firm way. The clip pivots around a pin 604 in which a top arm 606A and a bottom arm 602B are arranged to provide leverage to open and close the jaws. The front lower jaw includes an embedded finger sensor 610. The embedded finger sensor 610 may be similar to the sensor described in FIG. 5B. The embedded finger sensor 610 may include a membrane 612 configured to enclose a fluid 614. The membrane 612 may be constructed of a material such as rubber or plastic. The fluid 614 may be a liquid or a gel and may have a viscosity generally equivalent to that of human flesh. The back jaws 606A and 606B are kept apart (in order to apply a constant pressure on the finger 608) by a simple torsion spring or coiled spring (not shown in FIG. 6). The arms 606 are connected by a hinge pin which permits the motion in one direction only. The arms 606 should be rigid, but preferably made of a light weight material such as plastic. The jaws may be equipped with soft pads on one side of the hinge, where the device is clamped onto the body for comfort. The pads may be made of some flexible material such as foamed plastic.

The arms 606 may include a mechanism to provide a bias to apply a force on the upper jaw 602 such that the finger 608 is held in contact with the embedded finger sensor 610. The force applied is generally constant and may be accomplished by the use of a spring (a simple torsion spring or a coiled spring) to rotate the arms 606 about the hinge 604. Alternatively, the spring could be replaced by flexible bellows to which a controlled air pressure is applied. The use of a bellows has the advantage of precise adjustment, but requires an air supply source. Two strain gages 618A and 618B, one on each side, are affixed or glued to a platform 616 strip. As the platform moves under the pulses of blood pressure exerted on the membrane 612 and transferred by the fluid 614 to the platform 616, the bending of the platform 616 causes changes in the electrical resistance of the strain gages 618A and 618B, which then can be used to produce a blood pressure curve. The force or pressure applied to the finger by the arms and jaws is not large, for example the pressure may be less than 50% the diastolic blood pressure of the individual being monitored. An average diastolic pressure is approximately 78 mmHg. Due to the low force or pressure applied, the blood pressure may be monitored on a continuous basis.

This device is shown to be configured to monitor a finger, however other embodiments may be configured to be applied to many parts of the human body. For example, an ear lobe, a nose bridge, or a finger nail.

The measurement of changes in pressure is shown to be accomplished by use of dual strain gauges 618A and 618B. Dual strain gauges placed on either side of a platform 616 may be advantageous as one strain gauge is being stretched on one side, the other gauge is being compressed. This configuration provides greater accuracy. Also, the use of semiconductor strain gauges provides greater accuracy. It is recommended in certain situations to use polyimide film to affix or glue the strain gages 618 to the platform 616 for better stability. Also, in an alternative embodiment, a sensor assembly 610 may be affixed or glued directly to the nail using suitable type of glue.

Figure 7:
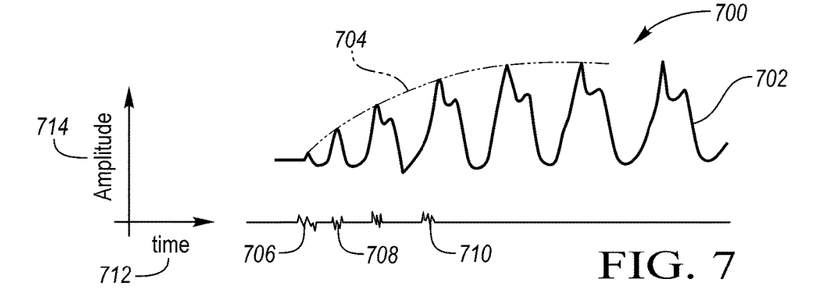
FIG. 7 is a graphical illustration of a blood pressure signal relative to time illustrating the effect of external pressure and the associated Korotkoff signal.

FIG. 7 is a graphical illustration of a signal from a sensor assembly in relation to time 712. Here, amplitude 714 of the effect of external pressure 704 on blood pressure signal 702 and the resulting Korotkoff sound pulses (706, 708, and 710) are illustrated in relation to time 712. For example, the signal growth curve method 700 may consist of a blood pressure waveform 702 from a sensor, such as a finger sensor on a finger of a left hand, the Korotkoff sound signal (line 706, 708, 710) from a diaphragm over a Brachial artery on the left arm, and the external pressure applied using a blood pressure cuff on the left arm. Curve 704 represents the envelope of consecutive blood pressure signals. Point in time 706 corresponds to systolic blood pressure and Point in time 710 corresponds to the diastolic blood pressure from the cuff method. Point 706 corresponds to the first appearance of a signal after releasing the pressure on the cuff from its maximum value. Point 710 corresponds to the first point in time where the blood pressure signal becomes generally constant.

The diastolic blood pressure may be determined using a Signal Growth Curve (SGC) method. An example of the SGC method is using a cuff around the upper left arm, and the pressure sensor device on a finger of the left hand. For example, an increase in pressure inside the cuff of 5 mmHg per sec may be used at a steady and slow rate. Once a diastolic blood pressure (Pd) is determined, it is recommended to decrease the pressure in the cuff to 10 mmHg below Pd and then repeat the process at the rate of 1mmHg per second for better accuracy for Pd. For each heartbeat, the area under the curve of the profile of the heartbeat is calculated.

At a low pressure inside the cuff, the area under the curve is the same for each heartbeat. For a specific heartbeat, the area under the curve may decrease by a predefined value. The diastolic pressure for that specific heartbeat is equal to the pressure inside the cuff at that point of time. A value of the diastolic pressure for the specific heartbeat is enough to configure the readings in the finger sensor. This method uses lower pressure than the regular cuff method because there is no need to cut the flow of the blood in the arm by exceeding the systolic blood pressure.

Figure 8A:
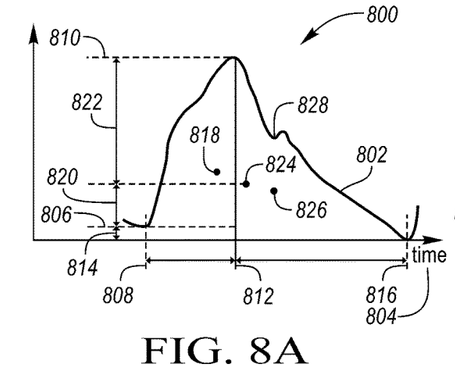
FIGS. 8A and 8B are graphical illustrations of a signal associated with a heartbeat from a sensor assembly in relation to time.
Figure 8B:
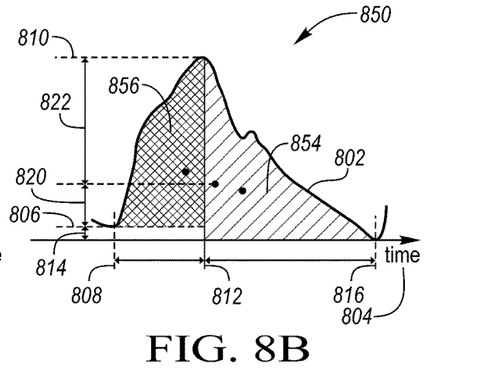

FIGS. 8A and 8B are graphical illustrations of a signal from a sensor assembly in relation to time. A profile of a blood pressure signal 800 includes a blood pressure signal 802 for a heartbeat in relation to time 804 that may be treated as a unit entity for the blood pressure waveform. Characterization of a single heartbeat requires isolation and recordation of the heartbeat. One method of isolating a heartbeat is to begin when the pressure signal reaches a relative minimum 806 (also referred to as a positive inflection point or a minima stationary point) at a point in time 808. The minimum 806 is associated with a diastolic blood pressure at the beginning of the heartbeat. After the relative minimum 806, the pressure will increase to a relative maximum at point 810 (also referred to as a negative inflection point or a maxima stationary point) at a point in time 812. The maximum 810 is associated with a systolic blood pressure. The signal will then drop to the relative minimum shown to be a small offset 814 from the previous minimum 806 and occurring at time 816. The minimum 816 is associated with a diastolic blood pressure at the end of the heartbeat. A first centroid may be determined for the time period between points 808 and 812 as shown by the point 818. A second centroid may be determined for the time period between points 812 and 816 as shown by the point 826. Also, a centroid may be determined for the complete heartbeat (the time period between point 808 and 816) as shown by point 824 is also referred to as MAP_c. The centroid is shown a distance 820 above the diastolic blood pressure and a distance 822 below the systolic blood pressure. When determining the relative maximums and minimums, it is important to use a proper window of time for determining the relative minimums and maximums. For example, if the window of time is too small, certain common aspects of a heartbeat such as an anacrotic notch between time 806 and 812 or a dicrotic notch 828 may be confused with the actual relative minimums and relative maximums. The dicrotic notch is associated with the closure of an aortic valve and provides a change in the waveform that may be detected as a relative minimum.

Figure 9:
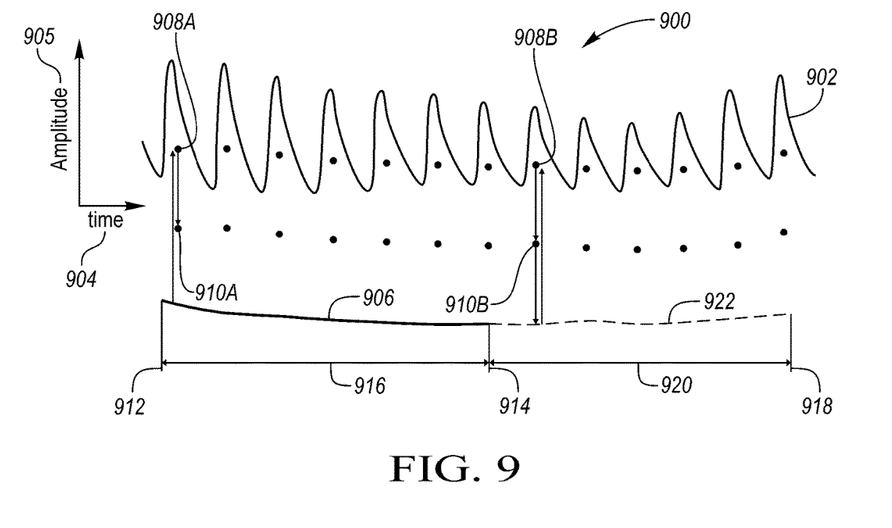
FIG. 9 is a graphical illustration of signals associated with mean arterial pressure (MAP) from a sensor assembly in relation to time.
Figure 12:
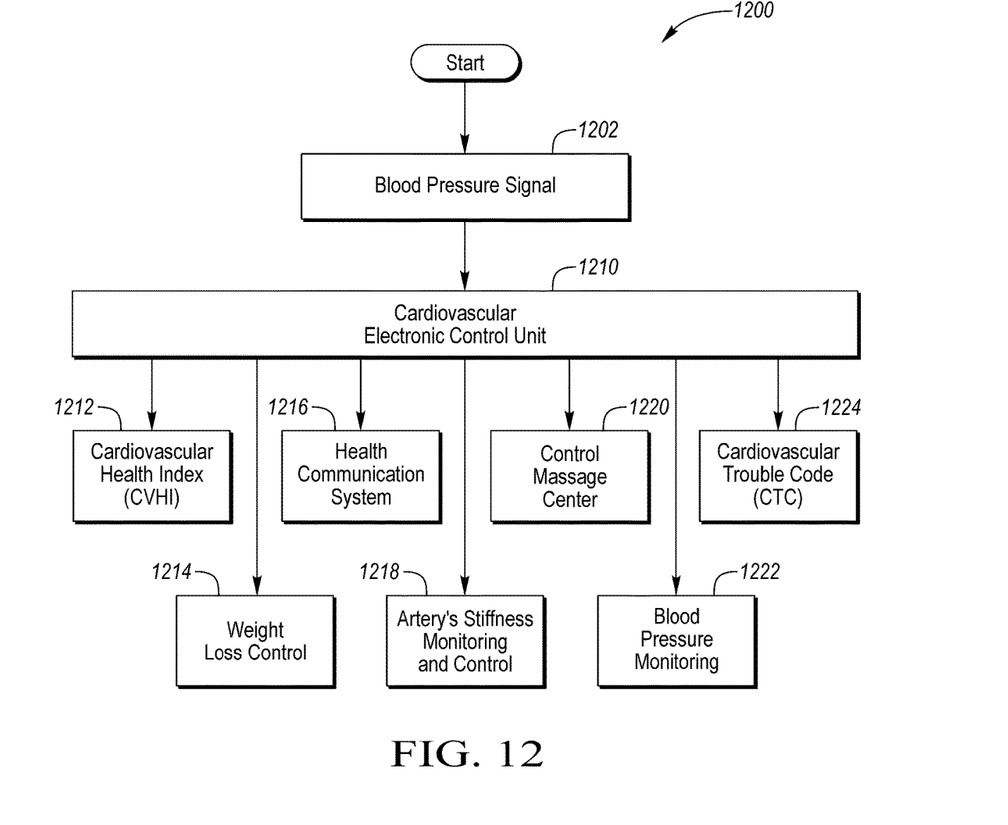
FIG. 12 is a flow diagram illustrating the output of cardiovascular characteristics from blood pressure waveform.

Parameters of a heartbeat may be used to determine a geometric index (SGI). The geometric index is shown in FIG. 9. Also, the parameters of a heartbeat may be used to generate a Cardiovascular Trouble Code (CTC) as shown in FIG. 12 below. Referring to blood pressure signal 800 and 850, the parameters include a mean arterial pressure associated with the centroid of the heartbeat (MAP_c). MAP_c is proportional to a rising area 856 as well as a falling area 854. The difference between rising area 856 and falling area 854 is proportional to an arterial resistance. Also, the difference between rising area 856 and falling area 854 is proportional to a change in MAP_c. The area under the curve (856 and 854) may be used to determine the systolic, diastolic and MAP.

The values of the parameters above can be used for the calibration for the sensors on the finger and/or the wrist with some correction factors (which can be determined experimentally). For example, the pressure under foot can be correlated to the pressure on the finger or on the wrist. The device readings may be validated at each beat of the heart. Also, device readings may be validated every 5 milliseconds. Moreover, a corrected reading should be displayed and used by the physicians, but the raw sensor readings should be stored for use by physicians and researchers for regression analysis. The validation should be based on the following:

The change in systolic pressure and diastolic pressure ($\Delta$P) is correlated to relative density of the pulsating mass under the curve. Hence, it will dictate the difference between diastolic pressure and MAP (based on the buoyancy principle of floating mass—similar to floating an ice cube in water). The body weight is correlated to MAP. The difference between rising area 856 and the falling area 854 is correlated to the MAP. An average heart beat rate should be between 40 and 200 beats per minute. The shape of the blood waveform should follow a specific shape, except for heart skipping beats or other diseases. A blood waveform is correlated to EKG signal. The change of blood pressure during the sampling time (for example a 5 millisecond sample time) for the device electronic controller unit (ECU) should be within a specific range value (like 1 mmHg). Statistical data analysis can be used for the blood pressure validation. The medical history of the patient can be used for validation. The correction of the waveform should be on both systolic and diastolic pressures and may require a translation and/or rescaling of the waveform for the corrected heartbeat. Also, long term device calibration and training is recommended.

For each heartbeat the CPU should associate the finger pulse waveform to the corresponding one from the foot pulse waveform. The finger diastolic pressure should be set equal to the value of foot diastolic pressure (finger Pd=foot Pd). Similarly, The finger systolic pressure should be set equal to the value of foot systolic pressure (finger Ps=foot Ps).

Some parameters available from the waveforms 800 and 850 include diastolic pressure at the start of the heartbeat signal (Pd1) 806, systolic pressure (Ps) 810, diastolic pressure at the end of the heartbeat signal (Pd2) 816, an area under the curve during the systolic phase (Area1) 856, an area under the curve during the diastolic phase (Area2) 854, centroid of Area1 (CG1) 818, centroid of Area2 (CG2) 826, change in diastolic pressure (H0) 814 (in which H0 is the amplitude at time 808—the amplitude at time 816), amplitude of heartbeat centroid (H1) 820 (in which H1 is MAP_c 824—Pd1 806), (H2) 822 (in which H2 is the systolic pressure (Ps) 810—MAP_c 824), systolic time (T1) (in which T1 is a time from Pd1 808 to Ps 812), and diastolic time (T2) (in which T2 is a time from Ps 816 to Pd2 812). From these parameters, additional parameters may be determined such as an Area12 index that equals Area1856/Area2 854, a H12 index=H1/H2, a T12 index=T1/T2, and a pulse pressure associated with the systolic pressure 810—diastolic pressure 806. These parameters may be calculated and recorded and used for long term calibration and validation, such as after the patient steps away from a bathroom scale configured with a sensor assembly.

FIG. 9 is a graphical illustration of a signal from a sensor assembly in relation to time. While the patient is standing on a scale, graphical illustration 900 visualizes the relation between MAP based on the centroid of the area under the curve (MAP_c) 908A, geometric shape index of blood pressure signal (SGI) 910A, and the MAP based on the body weight (MAP_w) 906. In this case if the difference between MAP_w and MAP_c exceeds a predefined value, then MAP_c should be set to MAP_w. Also, the device may be trained or calibrated for different body characteristics by measuring data such as body weight, body mass index, or while the patient performs an exercise such as deep breaths, or Valsalva maneuvers. Calibration data for MAP_c, MAP_w, and SGI may be saved in a lookup table. Once the patient steps off the scale, MAP_w should be read from the training lookup table based on the value of the MAP_c 908B and the SGI 910B for the corresponding heartbeat signal.

Figure 10:
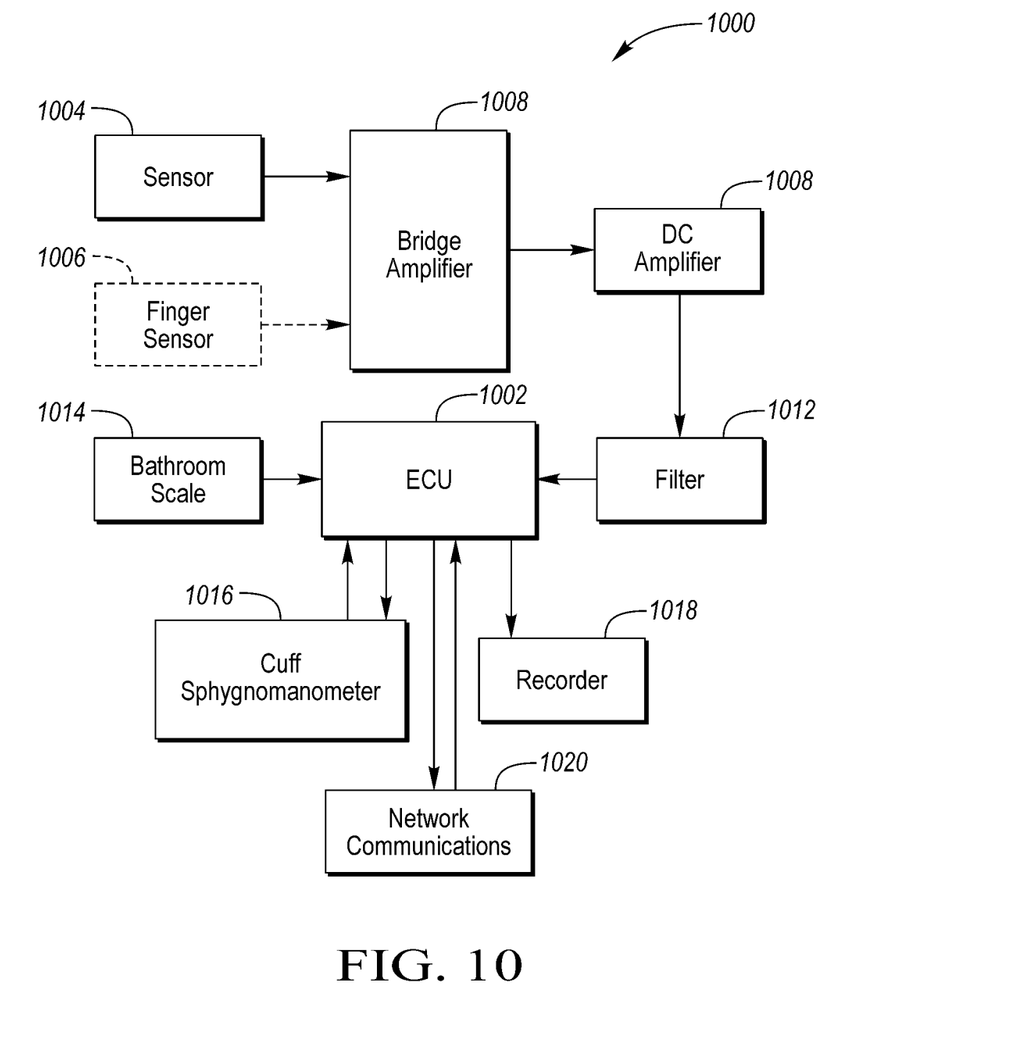
FIG. 10 is a block diagram of a non-invasive cardiovascular monitoring device configured to determine cardiovascular characteristics.

FIG. 10 is a block diagram of a non-invasive cardiovascular monitoring device 1000 configured to determine cardiovascular characteristics. The cardiovascular characteristics are calculated based on at least one of the data sources. Here, a sensor assembly 1004 may be used in which the sensor assembly 1004 may be attached to a human body. A finger sensor 1006 may be used. The sensor assembly 1004 and/or the finger sensor 1006 output a signal to a bridge amplifier 1008. The output from the bridge amplifier usually measured in microvolts is provided to a DC amplifier 1010. The DC amplifier amplifies the signal indicative of the blood pressure waveform to a range of millivolts. A filter 1012 is used to filter the signal. The filter 1012 may be a low pass filter filtering a range up to 25 hertz. The filter 1012 may be an analog filter or a digital filter. A digital filter may be an Infinite Impulse Response (IIR) filter or a Finite Impulse Response (FIR) filter. A filtered signal is received from an ECU 1002. The ECU 1002 may be a controller also referred to as a processor. The ECU 1002 may be coupled to a number of different types of serial, parallel, wireless or other data communication peripherals. The ECU 1002 may receive data from a scale 1014 such as a bathroom scale. The scale 1014 may provide a signal indicative of a weight of a patient. The weight of the patient from the scale 1014 used in combination with data from the sensor 1004 or the finger sensor 1006 may allow the ECU 1002 to calculate a mean arterial pressure (MAP). Also, the ECU 1002 may receive data from a cuff sphygmomanometer to calibrate the sensor 1004 or finger sensor 1006. The ECU may also communicate with a recorder 1018 and/or Network communications 1020. The recorder 1018 may include a visual display such as a LCD screen or a paper tape.

Figure 11A:
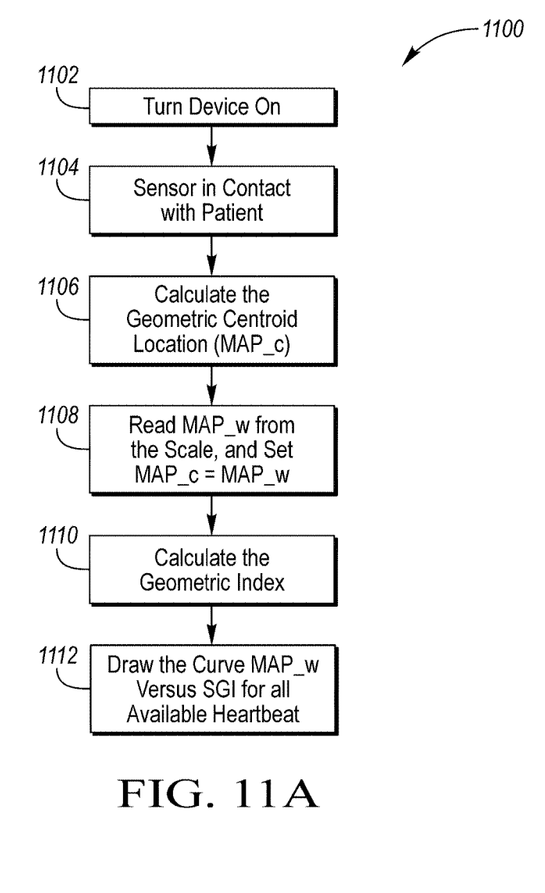
FIGS. 11A and 11B are flow diagrams that describe the logic to generate mean arterial pressure from a sensor assembly.
Figure 11B:
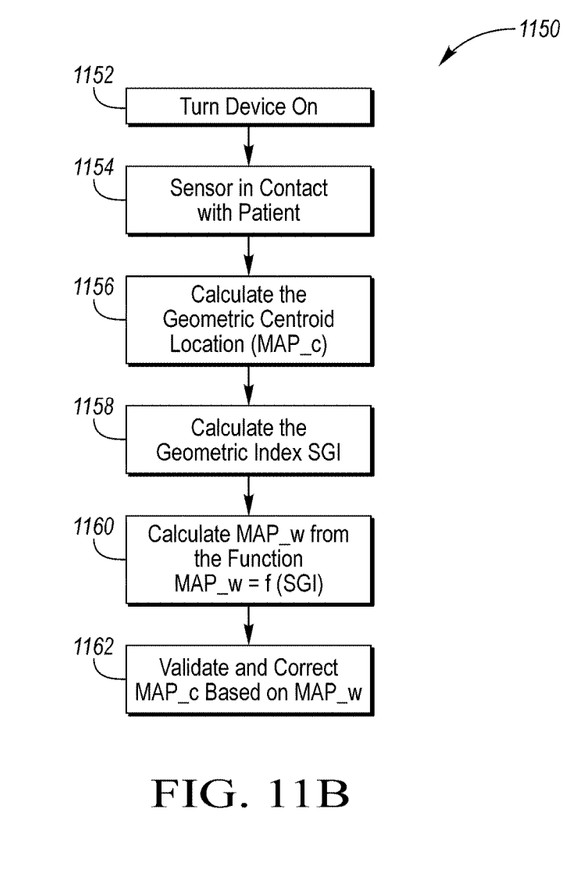

FIGS. 11A and 11B are flow diagrams capable of outputting a mean arterial pressure from a sensor assembly. FIG. 11A shows the flow diagram 1100 used when a patient is standing on a scale such as depicted in FIG. 1A or FIG. 1B.

In block 1102, the device is activated. In block 1104 a sensor assembly configured to measure a blood pressure using tonometry is pressed against a patient. The pressure applied to press the sensor assembly against the patient may be less than 50% of the diastolic pressure of the patient. The sensor assembly may be pressed against a patient in multiple locations including a finger, an arm such as an upper or lower arm, a leg such as a thigh or calf, a chest, a back, or an abdomen. In block 1106, a geometric centroid location (MAP_c) is calculated using a controller or processer. In block 1108, the mean arterial pressure based on weight (MAP_w) is input from the scale, and MAP_c is set to MAP_w. Here, MAP_w is calculated based on the signal from the scale. And MAP_c is validated and corrected based on MAP_w. In block 1110, a Signal Geometric Index (SGI) is determined by the controller or processor. The SGI that may be based on the parameters in FIG. 8 is determined. The SGI may be determined for each heartbeat or for a plurality of heartbeats. The SGI may include a numeric value, an alphanumeric code, a lookup table, or a graphical chart. The SGI may be used in a Cardiovascular Trouble Code (CTC). An example of a CTC is described in FIG. 12. In block 1112, the curve MAP_w versus SGI for all available heartbeats is determined. In other implementations, multiple heartbeats may be used in which many but not all heartbeats are used to generate this curve. The relationship of the data points (SGI, MAP_w) may be stored.

FIG. 11B shows a flow diagram 1150 in which patient blood pressure characteristics are already determined such as after the patient steps off the scale and data has been gathered such as illustrated in FIG. 1A. In block 1152, the device is activated. In block 1154 a sensor assembly configured to measure a blood pressure using tonometry is pressed against a patient. In block 1156, a geometric centroid location (MAP_c) is calculated using a controller or processer. In block 1158, the Signal Geometric Index (SGI) is used to calculate the mean arterial pressure based on geometric index (SGI). In block 1160, MAP_w is determined based on the function MAP_w=f(SGI). f(SGI) is shown in block 1112 of FIG. 11A. In block 1162, MAP_c is validated and corrected based on MAP_w.

FIG. 12 is a flow diagram illustrating a Cardiovascular Control System (CCS) 1200 that derives multiple characteristics of a patient from a blood pressure waveform of the patient. In block 1202, the blood pressure waveform is received by a controller or processor. In block 1210, a cardiovascular electronic control unit (CECU) decomposes the blood pressure signal into component signals using various signal processing techniques such as digital signal processing. The CECU outputs a Cardiovascular Health Index (CVHI) in block 1212. The CVHI includes indices such as central augmentation index and Peripheral augmentation index. The CVHI may also include all known health parameters like oxygen level and body temperature. CVHI is based on statistical data analysis and health risk factors. The CVHI may be used to select a recommended treatment for the patient or for preventive care.

The CECU outputs data to a Weight Loss Control block 1214. The exchange of nutrition and other particles between the blood stream and cells in the body depends on many aspects of a human body including the blood pressure. Therefore, one important clinical implication of the CECU is to provide data indicative of recommendations to implement a weight loss diet by controlling the blood pressure just before and after each meal. This can be achieved by physical exercise, medications, life style, and diet.

The CECU outputs data to a Health Communication System in block 1216. Many different malfunctions of the human body impact the blood pressure waveform. For example a missing heartbeat could lower diastolic pressure and extend a time period of that heartbeat. This CECU can detect the skipped heartbeat and can send a signal code to alert a physician of the skipped heartbeat. The CECU can detect signal codes by analyzing the medical and hemodynamic components of the blood pressure. Detecting the signal codes at early stage may improve chances to cure many diseases. Also, the Health Communication System 1216 may be used in communicating with vehicles and robot electronic components for the benefit of human beings. For example, the blood pressure device can detect early heart pain of a driving person and can call someone like EMS to help the driver.

The CECU outputs data to an Artery's Stiffness Monitoring and Control (ASMC) in block 1218. This is a similar to the CVHI of block 1212. However it is intended for use by healthy people to monitor the progress in controlling the stiffness of their arteries by physical exercises or following a certain diet. ASMC would encourage people to follow an exercise program by monitoring and plotting improvement in an ASMC index. Also, ASMC may be used by physicians in changing a recommended diet by assessing the improvement with respect to an expect result.

The CECU outputs data to a Control Massage Center block 1220. Controlled massage can be applied to various parts of the human body by the mean of a padding attachment. The padding attachment is placed proximate to a location of the body such as a back, an abdomen, or wrapped around an arm, leg, or abdomen. The padding attachment would apply pressure to stimulate and massage the body. The padding may be constructed of flexible tubes similar in size and flexibility to those of a human vascular system. A fluid would flow in the flexible tubes. The padding would allow control of the pulse rate, waveform, flow rate, and an electromagnetic waveform. An adaptive algorithm would then control the padding parameters based on blood pressure waveform and other parameters like body temperature to achieve the control of some cardiovascular parameters like blood pressure or blood flow.

The CECU outputs data to a Blood Pressure Monitoring (BPM) block 1222. In this block, the same functions as an invasive catheter may be employed to provide monitoring of the key parameters similar to that of the CVHI 1212 including the diagnosis of some diseases, preventative treatment, or clinical treatment. The advantage of this noninvasive device in performing the above functions includes less risk than invasive devices, easy to use, lower costs and greater comfort to the patient or healthy person or the physician.

The CECU outputs data to a Cardiovascular Trouble Code (CTC) block 1224. Any abnormality in the blood pressure waveform—like the absence of the dicrotic notch 828 that is a closure of aortic valve can be assigned a CTC number. Each CTC number should have a setting condition, including a possible root causes associated with the number. CTC 1224 can be used for the diagnosis of some diseases, or preventative treatment, or clinical treatment.

A CCS 1200 may be used at a medical facility and therefore may be used by multiple patients. One of the monitoring functions of the system may include collecting characterization information for each patient using it. The information may be stored in a database and archived for a patient's external diagnostic and prognostic uses. Physicians may then be able to assess each patient's health based on statistical analysis.

In the example of a CCS 1200 integrated into a scale and configured to be used in a home environment, the characterization information may be transmitted to a physician. The information may be analyzed by a server or other system based on a computer program, by the physician or other medical professional.

The processes, methods, or algorithms disclosed herein may be deliverable to or implemented by a processing device, controller, or computer, which may include any existing programmable electronic control unit or dedicated electronic control unit. Similarly, the processes, methods, or algorithms may be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms may also be implemented in a software executable object. Alternatively, the processes, methods, or algorithms may be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. A blood pressure sensor assembly comprising:
   a membrane having a surface configured for contact with a body of a patient;
   a liquid surrounded by the membrane and having a viscosity greater than 0.008 Poise;
   a substrate immersed in the liquid;
   a strain gauge mounted with the substrate such that changes in a contact pressure between the membrane and body due to changes in blood pressure associated with the body result in flexion of the substrate and changes in an output signal of the strain gauge; and
   a controller configured to output data indicative of changes in mean arterial pressure based on the changes in the output signal, and to output a subsequent mean arterial pressure based on an initial mean arterial pressure and a difference between consecutive centroids of a profile of the output signal indicative of a heartbeat while the contact pressure is less than 50 mmHg.

2. The assembly of claim 1, wherein the changes in the output signal define a pressure profile and wherein the changes in mean arterial pressure are derived from differences between maximum and minimum amplitudes of the profile.

3. The assembly of claim 1 further comprising
   a platform supporting the membrane; and
   a weight sensor coupled with the platform, and configured to output a weight signal based on a weight applied to the membrane, wherein the controller is further configured to output an initial mean arterial pressure based on the weight signal and the changes in the output signal.

4. The assembly of claim 3 further comprising a screen coupled with the platform, wherein the controller is further configured to output via the screen systolic and diastolic pressures based on the weight signal and the changes in the output signal.

5. The assembly of claim 3, wherein the controller is further configured to output a subsequent mean arterial pressure based on the initial mean arterial pressure and a difference between consecutive centroids of a profile of the output signal indicative of a heartbeat while the contact pressure is less than 50 mmHg.

6. The assembly of claim 1 further comprising another strain gauge, wherein at least a portion of the substrate is sandwiched between the strain gauges.

7. A blood pressure sensor assembly comprising:
   a gel having a viscosity greater than 0.008 Poise and being enclosed in a membrane;
   a base supporting the gel and configured to hold the gel against a person;
   a strain gauge assembly supported by the base, embedded in the gel, and configured to flex in response to pressure waves propagated by the gel due to changes in blood pressure associated with the person, and to output a signal indicative of the changes in blood pressure;
   a platform supporting the membrane;
   a weight sensor coupled with the platform and configured to output a weight signal based on a weight applied to the membrane; and
   a controller configured to output, based on the signal, a change in mean arterial pressure of the person, and to output a mean arterial pressure based on the weight signal and the signal indicative of the changes in blood pressure.

8. A blood pressure sensor assembly comprising:
   a membrane having a surface configured for contact with a body of a patient;
   a liquid surrounded by the membrane and having a viscosity greater than 0.008 Poise;
   a substrate immersed in the liquid;
   a strain gauge mounted with the substrate such that changes in a contact pressure between the membrane and body due to changes in blood pressure associated with the body result in flexion of the substrate and changes in an output signal of the strain gauge;
   a platform supporting the membrane;
   a weight sensor coupled with the platform, and configured to output a weight signal based on a weight applied to the membrane; and
   a controller configured to output data indicative of changes in mean arterial pressure based on the changes in the output signal, and to output an initial mean arterial pressure based on the weight signal and the changes in the output signal.

9. The assembly of claim 8 further comprising a screen coupled with the platform, wherein the controller is further configured to output via the screen systolic and diastolic pressures based on the weight signal and the changes in the output signal.

10. The assembly of claim 8, wherein the controller is further configured to output a subsequent mean arterial pressure based on the initial mean arterial pressure and a difference between consecutive centroids of a profile of the output signal indicative of a heartbeat while the contact pressure is less than 50 mmHg.

11. The assembly of claim 8 further comprising another strain gauge, wherein at least a portion of the substrate is sandwiched between the strain gauges.

\* \* \* \* \*